(12) United States Patent
Bookbinder et al.

(10) Patent No.: US 7,045,171 B2
(45) Date of Patent: May 16, 2006

(54) METHOD FOR FABRICATING SUPPORTED BILAYER-LIPID MEMBRANES

(75) Inventors: Dana C. Bookbinder, Corning, NY (US); Joydeep Lahiri, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 10/840,713

(22) Filed: May 5, 2004

(65) Prior Publication Data

US 2004/0213909 A1  Oct. 28, 2004

Related U.S. Application Data

(63) Continuation of application No. 10/228,862, filed on Aug. 27, 2002, now Pat. No. 6,756,078, which is a continuation of application No. 09/649,542, filed on Aug. 28, 2000, now Pat. No. 6,541,071.

(60) Provisional application No. 60/191,635, filed on Mar. 23, 2000.

(51) Int. Cl.
*B05D 1/36* (2006.01)
(52) U.S. Cl. ............... 427/407.2; 427/409; 427/412.1
(58) Field of Classification Search ............. 427/407.2, 427/409, 412.1
See application file for complete search history.

(56) References Cited

U.S. PATENT DOCUMENTS

| | | | |
|---|---|---|---|
| 5,242,828 A | 9/1993 | Bergström et al. | 435/291 |
| 5,512,131 A | 4/1996 | Kumar et al. | 156/655.1 |
| 5,624,711 A * | 4/1997 | Sundberg et al. | 427/261 |
| 5,741,409 A | 4/1998 | Raguse et al. | 204/296 |
| 5,763,191 A | 6/1998 | Knoll et al. | 435/7.1 |
| 5,798,030 A | 8/1998 | Raguse et al. | 204/403 |
| 5,834,224 A | 11/1998 | Ruger et al. | 435/14 |
| 5,840,083 A | 11/1998 | Bronislava et al. | 623/11 |
| 5,846,814 A | 12/1998 | Galla et al. | 435/287.2 |
| 5,922,594 A | 7/1999 | Löfäs | 435/291 |
| 6,048,546 A | 4/2000 | Sasaki et al. | 424/450 |
| 6,096,550 A | 8/2000 | Argo | 436/5 |
| 6,114,099 A | 9/2000 | Liu et al. | 430/324 |
| 6,180,288 B1 | 1/2001 | Everhart et al. | 430/2 |
| 6,228,326 B1 * | 5/2001 | Boxer et al. | 422/82.02 |
| 6,319,664 B1 * | 11/2001 | Bookbinder et al. | 435/4 |
| 6,329,209 B1 * | 12/2001 | Wagner et al. | 436/518 |

FOREIGN PATENT DOCUMENTS

WO  WO 96/10178  4/1996

OTHER PUBLICATIONS

Abdelghani et al, Materials Letters, 56(6), pp. 1064-1068, 2002.*
Schneider et al, Proceedings of SPIE, 4200, pp. 22-31, 2000.*

(Continued)

*Primary Examiner*—Erma Cameron
(74) *Attorney, Agent, or Firm*—David S. Resnick, Nixon Peabody LLP; Thomas R. Beall

(57) ABSTRACT

The present invention relates to a method and composition for producing a supported membrane. In one embodiment, the present invention relates to a method for producing a supported membrane comprising the steps: (i) providing a substrate coated with a monolayer having reactive functional groups; (ii) contacting the reactive groups with a linker compound to form a derivatized monolayer having covalently bonded linker moieties; and (iii) contacting the derivatized monolayer with a membrane solution to produce a supported membrane.

In a further embodiment, the present invention relates to a supported membrane produced by the methods of the present invention.

19 Claims, 5 Drawing Sheets

OTHER PUBLICATIONS

Carla A. Alves et al., "Atomic Scale Imaging of Alkanethiolate Monolayers at Gold Surfaces with Atomic Force Microscopy", J. Am. Chem. Soc. 1992, 114, p. 1222-1227.

Barbara J. Barner et al., "Polarization Modulation Fourier Transform Infrared Reflectance Measurements of Thin Films and Monolayers at Metal Surfaces Utilizing Real-Time Sampling Electronics", Anal. Chem. 1991, 63, pp. 55-60.

Christoph Bieri et al., "Micropatterned Immoblization of a G-Protein Coupled Receptor and Direct Detection of G Protein Activation", Nature Biotechnology, vol. 17, Nov. 1999, pp. 1105-1108.

Curtis W. Meuse et al., "Assessing the Molecular Structure of Alkanethiol Monolayers in Hybrid Bilayer Membranes with Vibrational Spectroscopies", Langmuir 1998, 14, p. 1604-1611.

Jay T. Groves et al., "Substrate-Membrane Interactions: Mechanisms for Imposing Patterns on a Fluid Bilayer Membrane", Langmuir 1998, 14, pp. 3347-3350.

Jay T. Groves et al., "Mcropatterning Fluid Lipid Bilayers on Solid Supports", Science, vol. 275, Jan. 31, 1997, pp. 651-653.

Paul S. Cremer et al., "Creating Spatially Addressed Arrays of Planar Supported Fluid Phospholipid Membranes", J. Am. Chem. Soc. 1999, 121, pp. 8130-8131.

Michael J. Green et al., "Real-Time Sampling Electronics for Double Modulation Experiments With Fourier Transform Infrared Spectrometers", Rev. Sci. Instrum. 62(6), Jun. 1991, pp. 1426-1430.

P. Harder et al., "Molecular Conformation in Oligo(ethylene glycol)-Terminated Self-Assembled Monolayers on Gold and Silver Surfaces Determines Their Ability To Resist Protein Adsorption", J. Phys. Chem. B 1998, 102, pp. 426-436.

Jennifer S. Hovis et al., "Patterning Barriers to Lateral Diffusion in Supported Lipid Bilayer Mebranes by Blotting and Stamping", Langmuir 2000, 16, pp. 894-897.

J.B. Hubbard et al., "Self assembly Driven by Hydrophobic Interactions at Alkanethiol Monolayers: Mechanism of Formation of Hybrid Bilayer Membranes", Biophysical Chemistry 75 (1998), pp. 163-176.

Joydeep Lahiri et al., "A Strategy for the Generation of Surfaces Presenting Ligands for Studies of Binding Based on an Active Ester as a Common Reactive Intermediate: A Surface Plasmon Resonace Study", Anal. Chem. 1999, 71, pp. 777-790.

Joydeep Lahiri et al., "Multi-Herne Self -Assmbly in Phospholipid Vesicles", J. Am. Chem. Soc. 1996, 118, pp. 2347-2358.

Holger Lang et al., A New Class of Thiolipids for the Attachment of Lipid Bilayers on Gold Surfaces, Langmuir 1994, 10, pp. 197-210.

Anne L Plant, "Supported Hybrid Bilayer Membranes as Rugged Cell Membrane Mimics", Langmuir 1999, 15, pp. 5128-5135.

Burkhard Raguse et al., "Tethered Lipid Bilayer Membranes: Formation and Ionic Reservoir Characterization", Langmuir 1998, 14, pp. 648-659.

M. Rueda et al., "Electrochemical Impedance Study of T1+ Reduction Through Gramicidin Channels in Self-Assembled Gramicidin-Modified Dioleoylphosphatidylcholine Monolayers on Mercury Electrodes", Langmuir 1999, 15, pp. 3672-3678.

Esa Stenberg et al., "Quantitative Determination of Surface Concentration of Protein With Surface Plasmon Resonance Using Radiolabeled Proteins", Journal of Colloid and Interface Science, vol. 143, No. 2, May 1991, pp. 513-526.

Claudia Steinem et al., "Impedance Analysis of Ion Transport Through Gramicidin Channels Incorporated In Solid Supported Lipid Bilayers", Bioelectrochemical and Bioenergetics 42 (1997), pp. 213-220.

Cindra A. Widrig et al., "Scanning Tunneling Microscopy of Ethanethiolate and $n$-Octadecanethiolate Monolayers Spontaneously Adsorbed at Gold Surfaces", J. of Am. Chem. Soc., vol. 113, No. 8, Apr. 10, 1991, pp. 2805-2810.

Lin Yan et al., "Formation and Reaction of Interchain Carboxylic Anhydride Groups on Self-Assembled Monolayers on Gold", Langmuir 1997, Vol. 13, No. 25, pp. 6704-6712.

Brink et al., Biochem. Biophys. Acta, 1196(2), pp. 227-230, 1994.

Duschl et al., Biophy. J., 67(3), pp. 1229-1237, 1994.

Scheibler et al., Polym. Bull. (Berlin), 40(2-3), pp. 151-157, 1998.

Vanderah et al., Langmuir, 16(16), pp. 6527-6532, 2000.

Lahiri et al., Langmuir, 16(20), pp. 7805-7810, 2000.

Krysinski et al., Langmuir, 17(13), pp. 3852-3857, 2001.

* cited by examiner

500 μm

METHOD FOR FABRICATING SUPPORTED BILAYER-LIPID MEMBRANES

CROSS-REFERENCE TO RELATED APPLICATION

The present application is a Continuation of U.S. Ser. No. 10/228,862 filed on Aug. 27, 2002, now issued U.S. Pat. No. 6,756,078, which is a Continuation of U.S. Ser. No. 09/649,542 filed on Aug. 28, 2000, now issued U.S. Pat. No. 6,541,071, which claims the benefit under 35 U.S.C. § 119(e) of U.S. Provisional Application No. 60/191,635, filed on Mar. 23, 2000.

BACKGROUND OF THE INVENTION

As a large fraction of drug targets are membrane bound proteins (e.g., G-protein coupled receptors, ion-channels, etc.), there is a need for the development of surfaces that bind lipids incorporating membrane bound targets. For example, bilayer-lipid membranes adsorbed onto solid supports, referred to as supported bilayer-lipid membranes, can mimic the structural and functional role of biological membranes. See Bieri, C. et al., *Nature Biotech*, 1999, 17, 1105–1108; Groves, J. T. et al., *Science* 1997, 275, 651–653; Lang, H. et al., *Langmuir* 1994, 10, 197–210; Plant, A. L. et al., *Langmuir* 1999, 15, 5128–5135; and Raguse, B. et al., *Langmuir* 1998, 14, 648–659. These hybrid surfaces were developed to overcome the fragility of black lipid membranes while preserving aspects of lateral fluidity observed in native biological membranes. The properties of supported membranes are determined by the nature of the adsorbing surface. Self-assembled monolayers may be used to coat a substrate and are capable of further derivatization to attach membranes.

Surfaces binding lipid membranes can be broadly classified into three categories: (i) hydrophobic surfaces (e.g., self-assembled monolayers presenting terminal methyl groups) which support the adsorption of lipid monolayers are of limited utility as they cannot be used to incorporate membrane-spanning proteins (Plant, A. L., *Langmuir* 1999, 15, 5128–5135); (ii) hydrophilic surfaces (e.g., glass surfaces) which bind bilayer-lipid membranes are also of limited utility as they can only be used to incorporate membrane-spanning proteins with extra-membrane domains that are less thicker than the layer of adsorbed water (~10° A) (Groves, J. T. et al., *Science* 1997, 275, 651–653; and Groves, J. T. et al., *Langmuir* 1998, 14, 3347–3350); and (iii) hybrid surfaces presenting amphiphilic anchor lipids that bind bilayer-lipid membranes offer the potential for incorporating a wide variety of membrane-spanning proteins (Lang, H. et al., *Langmuir* 1994, 10, 197–210; Raguse, B. et al., *Langmuir* 1998, 14, 648–659; and Vanderah, D. J. et al., *Materials Research Society Fall Meeting Abstracts*, Boston, 1999).

Self-assembled monolayers ("SAMs") of alkanethiolates on gold are well suited for studying biomolecular recognition at surfaces because the well-defined structures are amenable to detailed characterization at a molecular level (e.g., Scanning Tunneling Microscopy "STM," Atomic Force Microscopy "AFM," etc.). See Widrig, C. A. et al., *J. Am. Chem. Soc.* 1991, 113, 2805–2810; and Alves, C. A. et al., *J. Am. Chem. Soc.* 1992, 114, 1222–1227. They may also be addressed by a variety of bioanalytical techniques (e.g., optical, electrochemical, etc.). See Lahiri, J. et al., *Anal. Chem.* 1999, 71, 777–790; Plant, A. L., *Langmuir* 1998, 14, 3347–3350; Rueda, M. et al., *Langmuir* 1999, 15, 3672–3678; and Steinem, C. et al., *Bioelectrochem. and Bioenerg.* 1997, 42, 213–220.

The importance of a hydrophilic spacer between the substrate and the adsorbed lipid has been studied. The use of thiolated anchor lipids consisting of dipalmitoylphosphatidic acid extended at the hydrocarbon end by a hydrophilic ethyleneoxy group linked at the other end to a terminal disulfide has been shown (Lang, H. et al., *Langmuir* 1994, 10, 197–210; Plant et al., *Materials Research Society Fall Meeting Abstracts*, Boston, 1999; and Raguse et al., *Langmuir* 1998, 14, 648–659). Similar anchor lipids containing thiaoligoethyleneoxide ($HS(CH_2CH_2O)_n-$) moieties have also been used. However, these approaches have two disadvantages:

first, they require the laborious synthesis of the oligo(ethylene oxide) containing thiols, and second, the structures of the SAMs formed from these thiols may not be well-defined. Biotinylated anchor lipids have been used to immobilize streptavidin on self-assembled monolayers presenting biotin groups (Bieri, C. et al., *Nature Biotech*. 1999, 17, 1105–1108). Although this strategy circumvents issues regarding the structure and stability of putative self-assembled monolayers containing thiaoligoethyleneoxide moieties, the approach itself is cumbersome and requires the synthesis of biotinylated thiols. A simpler method for fabricating a supported membrane is desired.

Methods to create arrays of membranes would enable high-throughput screening of multiple targets against multiple drug-candidates. Arrays of membranes may be obtained by fabricating grids of titanium oxide on a glass substrate as titanium oxide resists the adsorption of lipids (Boxer, S. G. et al. *Science* 1997, 275, 651–653; and Boxer, S. G. et al. *Langmuir* 1998, 14, 3347–3350). Micropipeting techniques have been used to spatially address each corralled lipid-binding region (Cremer, P. S. et al., *J. Am. Chem. Soc.* 1999, 121, 8130–8131). However, these methods are cumbersome and require the fabrication of patterned surfaces. To make membrane arrays by printing membranes on unpatterned surfaces, it would be necessary to confine the membrane to the printed areas without lateral diffusion of the membrane molecules to the unprinted areas. Boxer et al. demonstrated that it was possible to pattern lipids on glass surfaces by microcontact printing using poly-dimethylsiloxane (PDMS) stamps "inked" with phosphatidylcholine ("PC"). They attributed the lateral confinement of the lipids to the stamped regions, to the self-limiting expansion of PC membranes to ~106% of the original printed areas (Hovis, J. et al., *Langmuir* 2000, 16, 894–897).

SUMMARY OF THE INVENTION

The present invention relates to a method and composition for producing a supported membrane. In one embodiment, the present invention relates to a method for producing a supported membrane comprising the steps: (i) providing a substrate coated with a monolayer having reactive functional groups; (ii) contacting the reactive groups with a linker compound to form a derivatized monolayer having covalently bonded linker moieties; and (iii) contacting the derivatized monolayer with a membrane solution to produce a supported membrane.

In another embodiment, the present invention relates to a method for producing a supported membrane comprising the steps: (i) providing a substrate coated with a monolayer having reactive functional groups; (ii) activating the reactive functional groups on the monolayer coated substrate to form an activated monolayer; (iii) contacting the activated monolayer with a linker compound to form a derivatized monolayer having covalently bonded linker moieties; and (iv) contacting the derivatized monolayer with a membrane solution to produce a supported membrane.

In yet another embodiment, the present invention relates to a method of producing a supported membrane comprising the steps: (i) providing a gold substrate coated with a monolayer having carboxylic acid groups; (ii) activating the carboxylic acid groups to form an activated monolayer having anhydride groups; (iii) contacting the activated monolayer with a linker compound to form a derivatized monolayer having covalently bonded linker moieties; and (iv) contacting a membrane solution with the derivatized monolayer to produce a supported membrane.

In a further embodiment, the present invention relates to a supported membrane produced by any of the methods of the present invention.

The method of the present invention offers several advantages over the previous approaches: (i) the method requires minimal organic synthesis as most of the reagents are commercially available; (ii) the method uses a reactive intermediate onto which any potential linker moiety with a terminal nucleophilic functional group can be attached; the use of a common reactive intermediate obviates the need for the individual synthesis of thiolated linker moieties; (iii) the method separates the covalent attachment of the linker moiety from the initial formation of a well-defined and stable monolayer; and (iv) the method allows control of the surface density of the adsorbed membrane, where the adsorbed membranes retain natural form and function.

DETAILED DESCRIPTION

Figure 1:
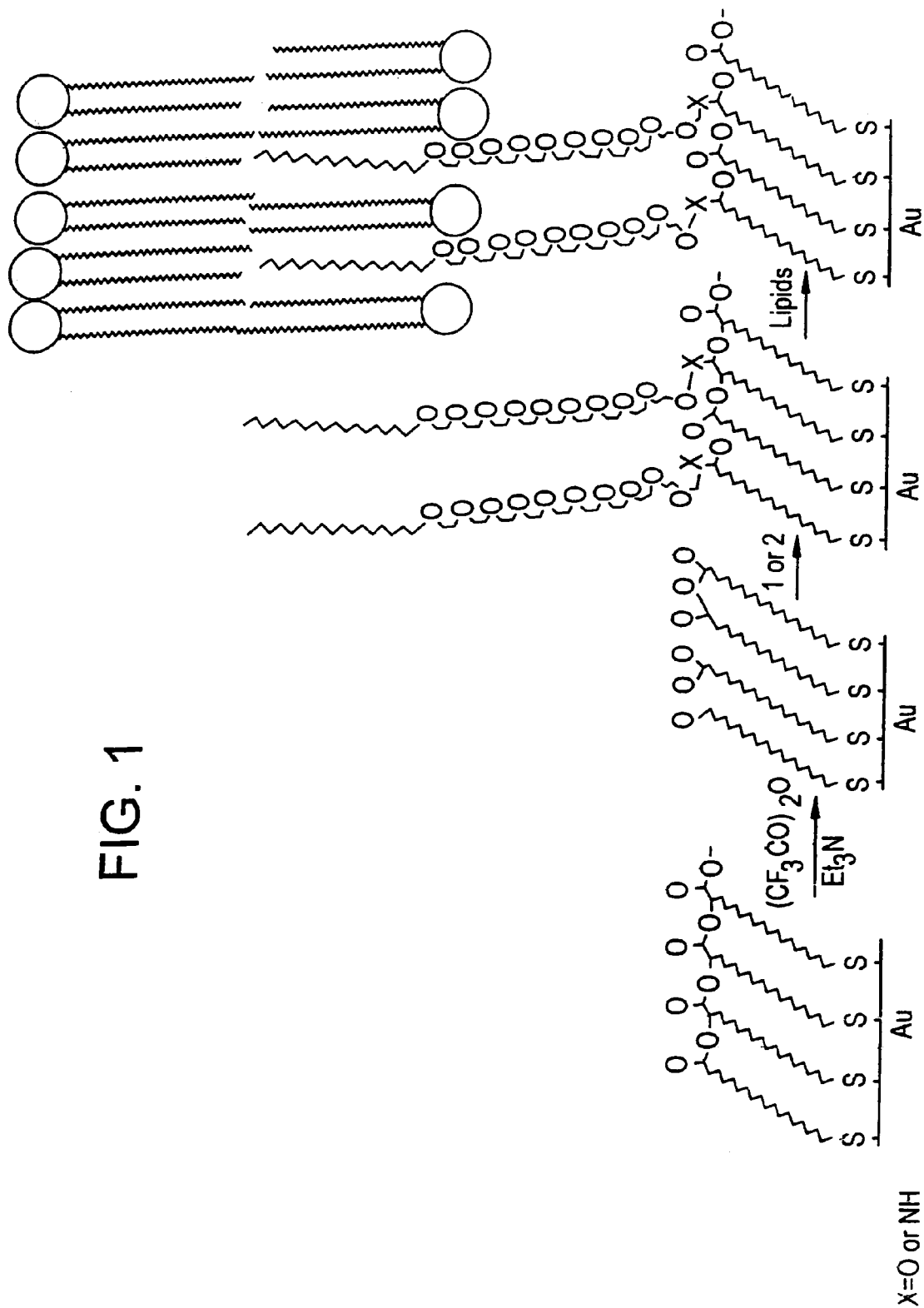
FIG. 1 shows a schematic representation showing the formation of supported bilayer-lipid membranes ("sBLMs") on gold. SAMs of 16-mercaptoahexadecanoic acid ("MHA") on gold were activated by trifluoroacetic anhydride and triethylamine, and the activated SAMs were immersed in solution A (20 mg mL−1; 28 mM; catalytic amount of DMAP) or B (10 mg mL−1; 14 mM in anhydrous NMP containing 0.5% triethylamine). The Brij®-derivatized SAMs were then immersed in a solution of lipids (phosphatidylcholines) to form the sBLM.

The present invention relates to a method and composition for producing a supported membrane. This invention relates to the surfaces for membrane adsorption that are well defined on a molecular scale, are synthetically convenient to execute, can be potentially tailored to incorporate membranes of different thicknesses, are amenable to detailed characterization by a variety of bioanalytical methods (for example, Infrared Spectroscopy, Surface Plasmon Resonance etc.), and can be potentially used for conveniently printing high density arrays ("HDAs") of membranes. This invention further relates to the use of a commercial HDA printer (for example, but not limited to, quill-pin printer) or standard incubation techniques for arraying membranes and for making membrane arrays on substrates. These methods facilitate the creation of convenient to use, high-throughput tools for screening against membrane bound targets.

The present invention relates to a method and composition for producing a supported membrane. In one embodiment, the present invention relates to a method for producing a supported membrane comprising the steps: (i) providing a substrate coated with a monolayer having reactive functional groups; (ii) contacting the reactive groups with a linker compound to form a derivatized monolayer having covalently bonded linker moieties; and (iii) contacting the derivatized monolayer with a membrane to produce a supported membrane.

In another embodiment, the present invention relates to a method for producing a supported membrane comprising the steps: (i) providing a substrate coated with a monolayer having reactive functional groups; (ii) activating the reactive functional groups on the monolayer coated substrate to form an activated monolayer; (iii) contacting the activated monolayer with a linker compound to form a derivatized monolayer having covalently bonded linker moieties; and (iv) contacting the derivatized monolayer with a membrane solution to produce a supported membrane.

In yet another embodiment, the present invention relates to a method of producing a supported membrane comprising the steps: (i) providing a gold substrate coated with a monolayer having carboxylic acid groups; (ii) activating the carboxylic acid groups to form an activated monolayer having anhydride groups; (iii) contacting the activated monolayer with a linker compound to form a derivatized monolayer having covalently bonded linker moieties; and (iv) contacting a membrane solution with the derivatized monolayer to produce a supported membrane.

In a further embodiment, the present invention relates to a supported membrane produced by any of the methods of the present invention.

Substrates are any desired dimensionally stable solids which may consist of a ceramic substance, a glass, a metal, a crystalline material, a plastic, a polymer or co-polymer, any combinations thereof, or a coating of one material on another. For example, but not limited to, (semi) noble metals such as gold or silver; glass materials such as soda glass, pyrex glass, vycor glass, quartz glass; metallic or non-metallic oxides; silicon, monoammonium phosphate, and other such crystalline materials; transition metals; plastics or polymers, including dendritic polymers, such as poly(vinyl chloride), poly(vinyl alcohol), poly(methyl methacrylate), poly(vinyl acetate-maleic anhydride), poly(dimethylsiloxane) monomethacrylate, polystyrenes, polypropylene, polyethyleneimine; copolymers such as poly(vinyl acetate-co-maleic anhydride), poly(styrene-co-maleic anhydride), poly(ethylene-co-acrylic acid) or the like. In a preferred embodiment, the substrate may be modified to enable the immobilization of biological molecules, for example, but not limited to, coating with gold or silver, formation of a patterned surface etc.

The monolayer coating, for example, comprising of long chain hydrocarbon moieties, on the substrate may have for example, but not limited to, thiol, disulfide or silane groups that produce a chemical or physicochemical bonding to the substrate. The attachment of the monolayer to the substrate may also be achieved by non-covalent interactions or by covalent reactions. For example, but not limited to, vinyl groups on a solid substrate could be copolymerized with a vinyl-terminated molecule on the monolayer; a sulphur-terminated molecule on the monolayer could be adhered to a metal (e.g., gold or silver) substrate; or condensation or addition reactions could be used to anchor the monolayer.

In accordance with the present invention, after attachment to the substrate the monolayer has at least one reactive functional group. Examples of reactive functional groups on the monolayer coating are, but not limited to, carboxyl, isocyanate, halogen, amine or hydroxyl groups. In one embodiment, these reactive functional groups on the monolayer coating may be activated by standard chemical techniques to corresponding activated functional groups on the monolayer coating (for example, conversion of carboxyl groups to anhydrides or acid halides, etc.). The activated functional groups of the monolayer coating on the substrate may be, but not limited to, anhydrides, N-hydroxysuccinimide esters or other common activated esters or acid halides, for covalent coupling to terminal amino groups of the linker compound. In another embodiment, the activated functional groups on the monolayer coating may be, but not limited to, anhydride derivatives for coupling with a terminal hydroxyl group of the linker compound; hydrazine derivatives for coupling onto oxidized sugar residues of the linker compound; or maleimide derivatives for covalent attachment to thiol groups of the linker compound. In a preferred embodiment, of the present invention, at least one terminal carboxyl group on the monolayer coating is first activated to an anhydride group and then reacted with a linker compound to form a derivatized monolayer coating, i.e., derivatized with a linker moiety.

In a second embodiment, the reactive functional groups on the monolayer coating may be reacted with a linker compound having activated functional groups, for example, but not limited to, N-hydroxysuccinimide esters or acid halides for covalent coupling to reactive amino groups on the monolayer coating.

The linker compound has one terminal functional group, a spacer region and a membrane adhering region. The terminal functional groups for reacting with the activated functional groups on the activated monolayer coating are for example, but not limited to, halogen, amino, hydroxyl, or thiol groups. The spacer region may consist of, but not limited to, oligo/poly ethers, oligo/poly peptides, oligo/poly amides, oligo/poly amines, oligo/poly esters, oligo/poly saccharides, polyols, multiple charged species or any other combinations thereof. For example, but not limited to, oligomers of ethylene glycols, peptides, glycerol, ethanolamine, serine, inositol, etc., and is such that membranes freely adhere to the membrane adhering region of the linker moiety. The spacer region may be hydrophilic in nature. In one preferred embodiment, the spacer has n oxyethylene groups, where n is between 2 and 25. In the most preferred embodiment, the spacer has ten oxyethylene groups. In a preferred embodiment the membrane adhering region or "hydrophobic tail" of the linker compound is hydrophobic or amphiphilic with straight or branched chain alkyl, alkynyl, alkenyl, aryl, araalkyl, heteroalkyl, heteroalkynyl, heteroalkenyl, heteroaryl, or heteroaraalkyl. In a preferred embodiment, the membrane adhering region comprises of a $C_{10}$ to $C_{25}$ straight or branched chain alkyl or heteroalkyl hydrophobic tail. In the most preferred embodiment, the hydrophobic tail comprises a $C_{10}$ to $C_{20}$ straight or branched chain alkyl fragment.

Figure 5:
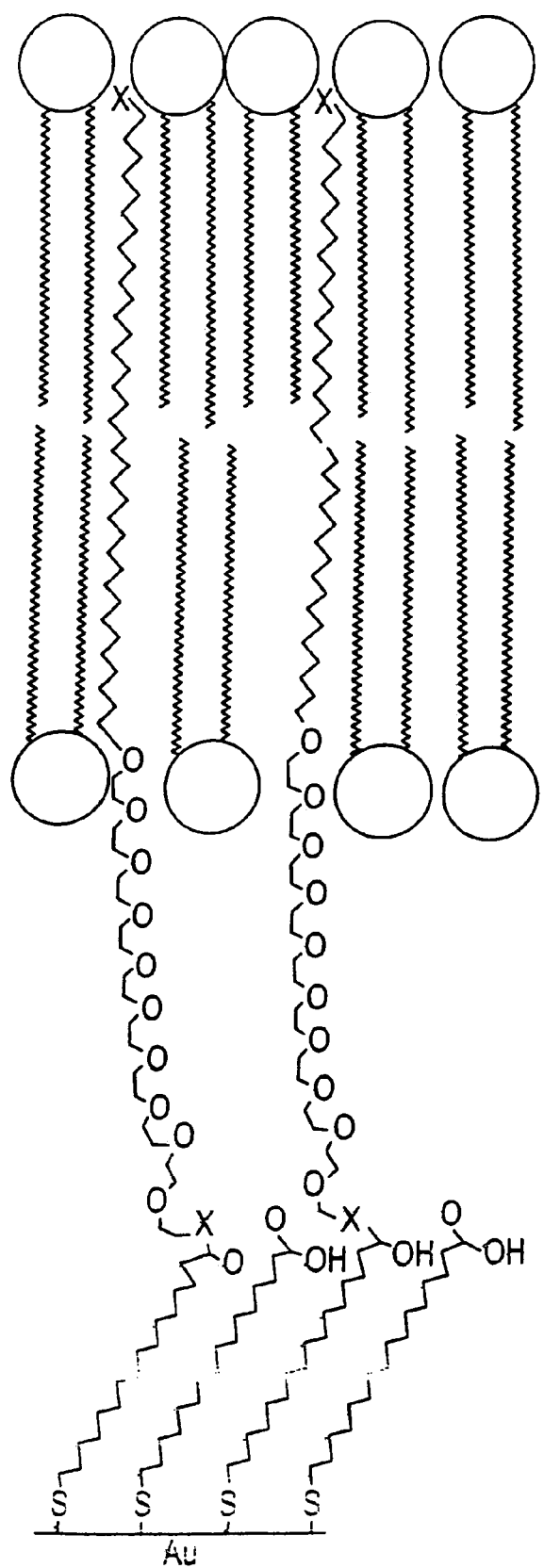
FIG. 5 shows a schematic representation of one embodiment of the invention wherein a hydrophilic group "x" is at one end of the membrane adhering region or hydrophobic tail.

In another embodiment, the linker compound has a terminal functional group on one end, a spacer, a membrane adhering region and a hydrophilic group on another end (FIG. 5). The hydrophilic group at one end of the linker compound may be a single group or a straight or branched chain of multiple hydrophilic groups. For example, but not limited to, a single hydroxyl group or a chain of multiple ethylene glycol units.

In accordance with the present invention, the method of producing a supported membrane has several advantages: (i) the initial monolayer consists of one type of molecule, which removes issues regarding the surface mole fraction of reactive functional groups that may be activated to form activated functional groups if required; (ii) the selected reactive groups or the activated functional groups are highly reactive and may therefore be used for conjugation to linker compounds; and (iii) the surface density of the covalently bonded linker moieties can be varied by controlling the immersion time of the derivatized or activated monolayer in the solution containing linker compounds, or by mixing the solution containing linker compounds with auxiliary nucleophiles (e.g., ethanolamine; for example, but not limited to, an achievable surface density of 50%). A very high-density of lipid could sterically prevent the insertion of the membrane onto the linker moiety derivatized monolayer. In one embodiment of the method of the present invention, the strategy for activation involves the formation of a reactive interchain anhydride (Yan et al., *Langmuir* 1997, 13, 6704–6712).

In accordance with the present invention, at least one membrane is adsorbed on the lipid moiety derivatized monolayer coating by printing or incubation using standard incubation techniques or printers (for example, quill-pin printers). The ability to print lipids enables the development of HDAs of supported membranes for applications relating to high-throughput screening against membrane bound targets. HDAs of, for example, but not limited to, DNA, proteins, and cells immobilized on planar solid substrates (or "chips") offer tremendous possibilities for high-throughput screening of multiple targets against multiple drug-candidates, thereby greatly accelerating the process of drug discovery. In one embodiment of the present invention, HDAs of membrane proteins may be made in basically two ways: (i) by making substrates with patterned surfaces that are lipid-binding and lipid non-binding respectively, followed by addition of different membrane bound targets to each corralled lipid binding region; and (ii) by making substrates presenting surfaces that are completely lipid-binding, followed by printing of different membranes on the surface.

"Membrane solution" as referred to in the present invention comprises of a membrane which may be synthetic or naturally occurring, for example, but not limited to, vesicles, liposomes, monolayer lipid membranes, bilayer-lipid membranes, membranes incorporated with receptors or the like. Membranes suitable for use with the present invention are amphiphilic molecules, for example, but not limited to, phospholipids, sphingomyelins, cholesterol or their derivatives. In a preferred embodiment, the membrane is a bilayer-lipid that simulates a natural cell membrane and may be of varied lengths. In a further embodiment, the membrane may include a membrane-protein. Such membrane proteins include, for example, integral membrane proteins, peripheral membrane proteins and receptors (e.g., G protein-coupled receptors, ion-channel receptors, tyrosine kinase-linked receptors, cytokine receptors, and receptors with intrinsic enzymatic activity). In another embodiment, the membrane may be bilayer-lipid membranes incorporated with, but not limited to, ionophores (for example, but not limited to, valinomycin, nonactin, methyl monesin, coronands, cryptands or their derivatives), ion-channels (for example, but not limited to, protein ionophores, etc.) or synthetic or naturally occurring analytes, for example, but not limited to, antibody, enzyme, lectin, dye, chelating agent and the like.

In an additional embodiment, the present invention can be used to produce an array of cells. For example, a ligand can be incorporated into the membrane and used to link a cell expressing the ligand receptor to the membrane. Conversely, the membrane can incorporate the receptor and the ligand expressed by the cell.

In the most preferred embodiments of the present invention, the method (as shown in FIG. 1) involves: (i) the formation of a self-assembled monolayer ("SAM") of 16-mercaptohexadecanoic acid ("MHA") on gold; (ii) the activation of the carboxylic acid groups to interchain anhydrides; (iii) the treatment of the reactive surfaces with Brij®-76-OH ($C_{18}H_{37}(OCH_2CH_2)_{n-10}OH$; "1") or Brij®-76-NH$_2$ ($C_{18}H_{37}(OCH_2CH_2)_{n-10}NH_2$; "2"); and (iv) formation of supported membranes on the Brij-derivatized surface by incubation or printing. The oligo(ethylene glycol)-stearyl moiety acts as the linker moiety and provides a hydrophilic spacer between the SAM coating on the substrate and the adsorbed lipid (for example, but not limited to, bilayer-lipid membranes, adsorbed vesicles, multilayered membranes, with or without associated proteins and ionophores).

Figure 2:
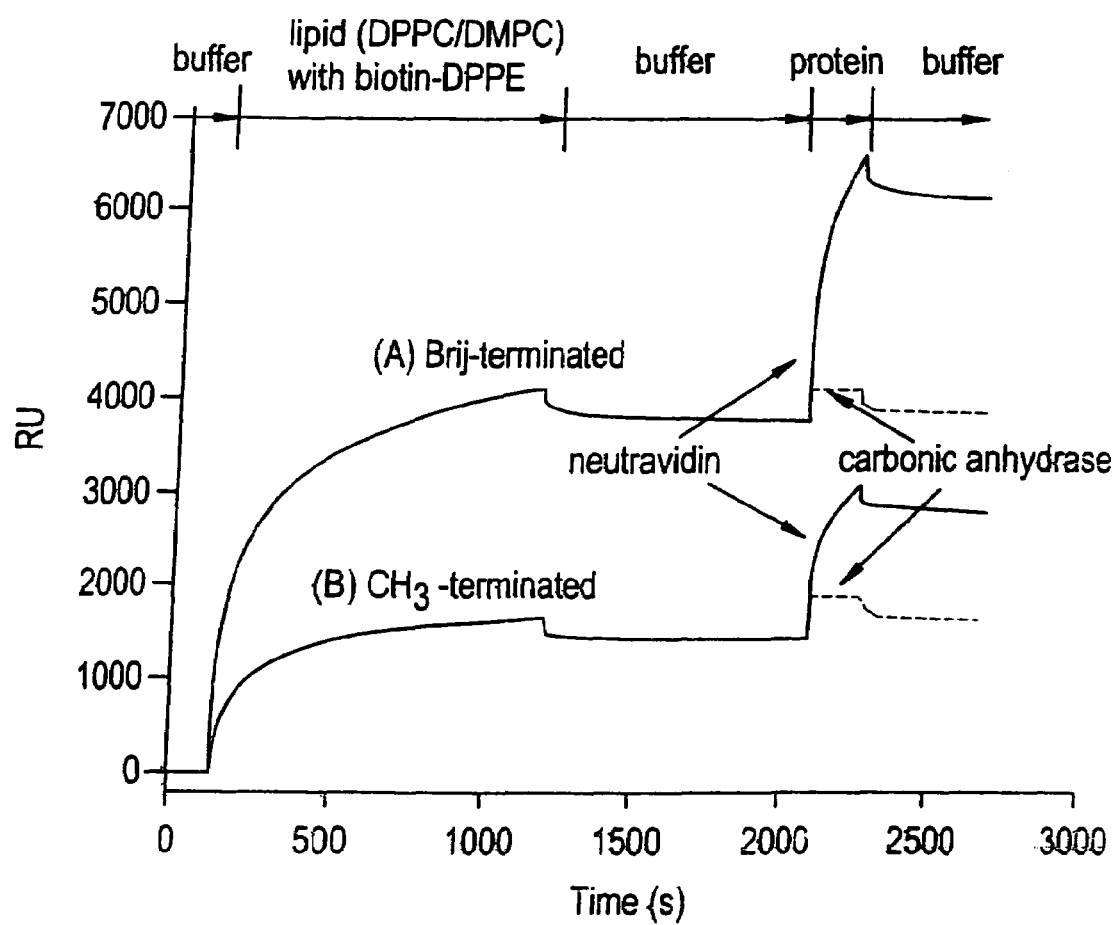
FIG. 2 shows SPR sensorgrams showing binding of PC lipids doped with DPPE-biotin to: (A) hexadecanethiolate-SAMs, and (B) MHA-SAMs derivatized with Brij®-76-NH$_2$, and the subsequent binding of neutravidin(−) and CA ( - - - ) to these surfaces.
Figure 3:
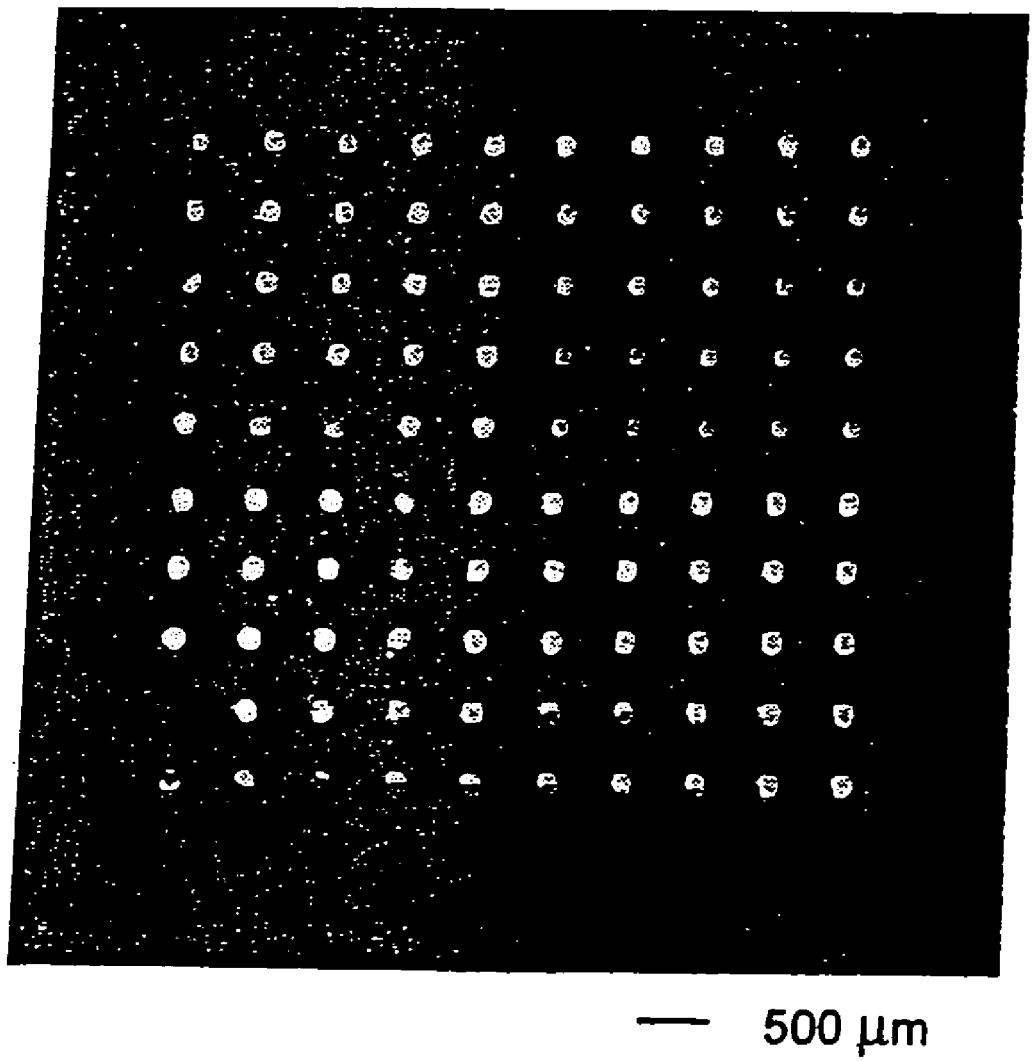
FIG. 3 shows a fluorescence micrograph of lipids (DPPC/DMPC/FITC-DHPE) printed in a 10×10 grid on a Brij®-derivatized gold surface, followed by incubation of the printed substrate under a solution of phosphate buffer (10 mm, pH=7.6) for 30 mins. The center-to-center distance between two spots is 500 Tm and remains constant over the time period of the experiment (3 hrs).
Figure 4:
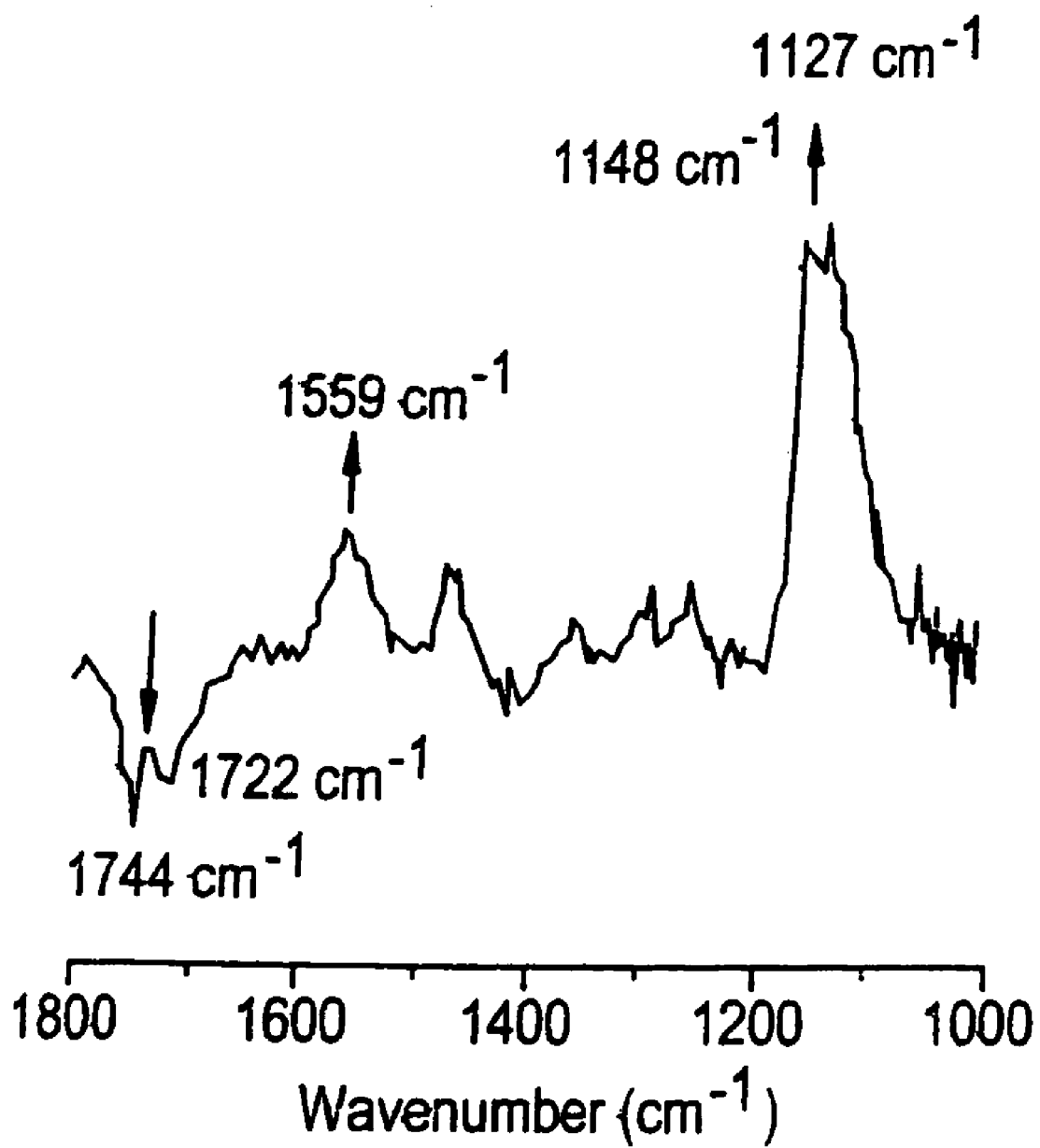
FIG. 4 shows a FTIR-difference spectrum between a MHA-SAM coated substrate with Brij®-76-NH$_2$, and the original MHA-SAM coated substrate.

IR spectroscopy was used to characterize the covalent attachment of the linker moiety to the SAM coating on the substrate to the MHA surface (FIG. 4). Surface plasmon resonance was used to compare the lipid-binding ability of the Brij-derivatized surface with that of a methyl-terminated SAM (FIG. 2). Using a conventional quill-pin printer, lipids were printed onto the linker moiety derivatized SAM coating on the substrate (FIG. 3). This demonstrates the feasibility of using conventional HDA printing technology in accordance with the present invention for making high-density membrane arrays.

In the following, the invention is illustrated by a non-limiting Exemplification which describes the method of the invention.

EXEMPLIFICATION

Materials 1 (Brij®-76-OH), 16-mercaptohexadecanoic acid (MHA), trifluoroacetic anhydride, triethylamine, dimethyl formamide (DMF), N-methylpyrrolidone (NMP), 4-(dimethylamino) pyridine (DMAP), tosyl chloride and sodium azide were obtained from Aldrich. L-I-dimyristoylphosphatidycholine (DMPC) and L-I-dipalmitoylphosphatidylcholine (DPPC) were purchased from Sigma or Avanti Polar Lipids. N-(fluorescein-5-thiocarbamoyl)-1,2-dihexadecanoyl-sn-glycero-3-phosphocthanolamine (fluorescein DHPE) was obtained from Molecular Probes. Neutravidin and DPPE-biotin were obtained from Pierce.

I. Synthesis of Brij®-76-amine ("2"):

The commercially available 1 was azeotroped in refluxing toluene to remove water. The dried 1 (5 g, 7.0 mmol) was then dissolved in methylene chloride; tosyl chloride (2.2 g, 11.5 mmol) in 4 mls of pyridine was added, and the solution stirred at room temperature for 24 h. After evaporation of the solvent, the crude Brij®-76-tosylate was stirred with sodium azide (4.55 g, 70 mmol) in DMF at 70° C. for 24 h. The solvent was removed under vaccuo. The material obtained was dissolved in chloroform, and undissolved materials were discarded. The chloroform was removed under vaccuo. The crude azide derivative was dissolved in methanol, and ~100 mg of Pd/C was added. The reduction of the azide to the amine was carried out under hydrogen for 48 h, using a Parr hydrogenator. The crude Brij®-76-NH$_2$ (2) was purified by flash chromatography using silica gel, eluting with chloroform/ methanol (9:1) to yield 2 in ~80% overall yield.

$^1$H NMR (300 MHz, CDCl$_3$): Λ 0.86 (t, 3H, J=7 Hz), 1.25 (m, 30 H), 1.55 (m, 2H), 3.13 (br t, 2H), 3.42 (t, 2H, J=6.8 Hz), 3.52–3.80 (m, 36 H), 3.86 (t, 2H, J=4.9 Hz). $^{13}$C NMR (300 MHz, CDCl$_3$): Λ 14.0, 22.6, 26.0, 29.3, 29.6, 31.9, 40.8, 67.7, 70.1, 70.5, 71.5.

II. Preparation of Brij®-Derivatized SAMs

The gold-coated slides, cleaned by soaking in a Piranha solution (70% conc. $H_2SO_4$, 30% $H_2O_2$) or used as supplied, were rinsed in absolute ethanol for 2 min, and dried under a stream of nitrogen. The slides were then immersed overnight in an ethanolic solution of MHA (2 mM). The slides were rinsed in ethanol, dried, and activated by immersion in a solution of 0.1 M trifluoroacetic anhydride and 0.2 M triethylamine in anhydrous DMF for 20 min. Thereafter, the slides were rinsed with methylene chloride and dried under a stream of nitrogen. These slides were immersed in a solution of A (20 mg mL$^{-1}$; 28 mM; catalytic amount of DMAP) or B (10 mg mL$^{-1}$; 14 mM in anhydrous NMP containing 0.5% triethylamine). After half an hour, the slides were rinsed thoroughly with ethanol, dried under a stream of nitrogen, and used for further experiments.

III. Covalent Binding of Brij®-76 Moiety to the Self-Assembled Monolayer of MHA (MHA-SAM)

Gold samples for Polarization Modular Fourier Transform Infrared Reflection Absorption Spectroscopy ("PM-FTIR-RAS") were prepared by vapor deposition of Cr (~5 nm) and gold (~100 nm) onto glass microscope slide covers (Fisher No. 2, 18×18 mm). Gold surfaces were modified with a SAM of MHA by soaking overnight in a 1 mM ethanolic solution of 16-mercaptohexadecanoic acid. The slides were thoroughly rinsed with absolute ethanol and water, and then dried under a stream of nitrogen. These surfaces were then activated by immersion in a solution containing trifluoroacetic anhydride (0.1 M) and triethylamine (0.2 M). These activated surfaces were then immersed in solutions of A (20 mg mL−1; 28 mM; catalytic amount of DMAP) or B (10 mg mL−1; 14 mM in anhydrous NMP containing 0.5% triethylamine).

PM-FTIRRAS measurements were obtained from a Matteson RS-1 spectrometer with real-time interferogram sampling electronics (Synchronous Sampling Demodulation Box, GWC Instruments) at an incident angle of 76°. See Green, M. J. et al., *Rev. Sci. Instrum.* 1991, 62, 1426–1430; Barner, B. J. et al., *Anal. Chem.* 1991, 63, 55–60. Prior to the sample, the FTIR beam passed through a wire grid polarizer set at p-polarization and then was sent through a 50 kHz ZnSe photoelastic modulator (Hinds). After the sample, the beam was collected with a ZnSe lens, and then focused onto a narrow-band HgCdTe detector. All spectra were collected from 1000 scans at 2 cm$^{-1}$ resolution.

FIG. 4 shows the PM-FTIRRAS difference spectrum between the Brij®-derivatized SAM and the initial MHA-SAM. The spectrum shows a decrease in the peak intensities at 1744 cm$^{-1}$ and 1722 cm$^{-1}$, which are assigned to the free and hydrogen bonded carboxylic acid stretches, respectively. The spectrum also shows the development of a peak at 1559 cm$^{-1}$, which can be assigned to an amide II band; the appearance of this band confirms the covalent attachment of 2 to the MHA-SAM through the formation of amide bonds. In addition, the appearance of bands at 1148 cm$^{-1}$ and 1127 cm$^{-1}$ assigned to the ethylene glycol C—O—C stretches confirm the presence of Brij® molecule on the surface. The presence of two different C—O—C bands indicate that both amorphous and helical ethylene glycol phases exist on the surface for SAMs containing oligo(ethylene glycol) groups. See Harder, P. et al, *J. Phys. Chem. B*. 1998, 102, 426–436. In order to characterize the reaction time dependence of 2 with MHA anhydride, we monitored the increase in the intensity of these ethylene glycol bands. Our experiments indicated that ~70% of the reaction was over within one minute.

PM-FTIRRAS measurements were also made on anhydride-modified surfaces that were reacted with 1 and a catalytic amount of DMAP. The reaction was monitored by following the development of bands due to the C—O—C stretch (at 1148 cm$^{-1}$); after ~2 hours the band initially was ~40% less than that observed for the corresponding reaction with 2.

IV. Adsorption of Bilayer-Lipid Membranes

Surface Plasmon Resonance ("SPR") was used to characterize the binding of lipids to the Brij®-derivatized surfaces with BIAcore 1000. SPR has been used to measure the intensity of reflection of monochromatic (760 nm for the BIAcore) p-polarized light incident on the back-side of a gold coated glass slide. Changes in the angle at which the intensity of reflected light is a minimum ($\Pi_m$) are related to changes in the index of refraction near the gold-solution interface (within approximately one-quarter wavelength (~200 nm) of the incident light). Within a family of similar compounds (e.g., lipids, proteins, etc.), changes in $\Pi_m$ correlate linearly with the mass per unit area of the adsorbed biomolecule. The BIAcore instrument reports changes in $\Pi_m$ in resonance units (RU; 10000 RU=–$\Pi_m$ 1°).

The binding of phospholipid vesicles to SAM derivatized with Brij®, and the capability of the resulting sBLMs to incorporate ligands for biospecific binding was studied. As an example, the interaction of avidin with supported membranes presenting biotin groups was studied. The biotin-avidin interaction is commonly used to test for biospecific binding; avidin binds biotin with very high affinity ($K^d$~10$^{-15}$ M) (Savage, D. et al, *Avidin-Biotin Chemistry: A Handbook*; Pierce Chemical Company: Rockford, Ill., 1994). The binding of vesicles to hexadecanethiolate-SAMs was used for comparison (Plant, A. L., *Langmuir* 1999, 15, 5128–5135; Hubbard, J. B. et al., *Biophys. Chem.* 1998, 75, 163–176).

The BIAcore 1000 instrument, used for all illustrated experiments, is equipped with an autosampler and was programmed for automatic handling of samples. Gold substrates for SPR were prepared by evaporating thin films of titanium (1.5 nm) and gold (40 nm) onto glass coverslips (0.2 mm, No. 2, Corning). These coverslips were cut into pieces ~10 mm×15 mm, and derivatized as described above. The derivatized gold substrates were glued into commercial CM5 cartridges from BIAcore (from which the entire gold-coated glass slide bearing the dextran was peeled off with a razor blade), and then docked into the BLAcore instrument.

Vials containing phosphate-buffered solutions (20 mM, pH 7.6) of the lipid (vesicles containing DMPC (0.21 mM), DPPC (1.35 mM), DPPE-biotin (0.18 mM), prepared by sonication), neutravidin (1.5 TM), and carbonic anhydrase (3.0 TM) were put in separate positions of the auto sampler tray. The gold surface was first equilibrated with the phosphate buffer (20 mM, pH 7.6) for 2 min. The solution of the biotin-doped lipid was then injected over the surface for 20 min. The system was then returned to the original phosphate buffer. After 15 min, the solutions of either neutravidin or carbonic anhydrase were injected over the lipid-modified surfaces for 3 mins. The system was again returned to the original buffer for 10 min.

FIG. 2 shows the binding of lipids consisting of DPPC and DMPC doped with amphiphilic biotin (DPPE-biotin) to Brij® derivatized MHA-SAM (FIG. 2, A) and methyl derivatized SAM (FIG. 2, B) presenting SAMs, and the binding of neutravidin (a deglycosylated analogue of avidin) to the surface-bound lipids. The amount of binding of lipid onto the Brij®-derivatized surfaces is ~4200 RU. A headgroup area of ~50 Å$^2$ per molecule for PC molecules in the condensed phase was assumed (Lahiri, J. et al., *J. Am. Chem. Soc.* 1996, 118, 2347–2358). The adsorption of a monolayer of DPPC/DMPC molecules corresponded to ~2.4 ng mm$^{-2}$ of adsorbed lipid. Assuming that the refractive index of the lipid is similar to that of protein (~1.45) (Lang, H. et al., *Langmuir* 1994, 10, 197–210; Hubbard, J. B. et al, *Biophys. Chem.* 1998, 75, 163–176) using the relation 1000 RU ~1 ng nm$^{-2}$ of adsorbed lipid (Steinberg, E. et al., *Colloid Interface Sci.* 1991, 143, 513–526) we estimate that the SPR signals corresponding to the adsorption of a liquid monolayer and bilayer-lipid membranes are 2400 RU and ~4800 RU, respectively. Our data therefore indicates the adsorption of a closely packed bilayer-lipid membrane on the Brij®-derivatized MHA-SAM surface. In contrast to the Brij®-derivatized MHA-SAM surface, the amount of adsorption of lipid on the methyl-terminated SAM surface was ~1750 RU, which is close to the expected value for the adsorption of the lipid monolayer, in agreement with previous observations (Plant, A. L., *Langmuir* 1999, 15, 5128–5135).

When neutravidin was injected over the adsorbed bionylated lipids, there were large increases in SPR signal indicative of binding of the protein to the surface, for both Brij® and methyl-terminated SAMs. In order to test whether the binding of neutravidin to the sBLMs presenting biotin groups was biospecific, carbonic anhydrase (CA) was injected/over the adsorbed lipids. CA has no known affinity for biotin or phosphatidylcholine lipids. The negligible amounts of binding of CA demonstrates that the binding of neutravidin to these surfaces was biospecific.

The SPR data described above is consistent with the adsorption of lipid-bilayers; this data does not exclude the possibility of other structures for the adsorbed lipids. For example, whole lipid vesicles and/or discontinuous multi-layered structures would also be consistent with the above data; for certain applications, it is possible that some of these structures (e.g. adsorbed whole vesicles) would be preferred over fluid lipid bilayers.

V. Printing of Lipids.

A quill-pin printer (Model PS 5000, Cartesian Technologies, Inc.) equipped with software for programmable aspiration and dispensing, was used for printing of lipids.

Solutions containing phosphatidylcholine vesicles (DPPC/DMPC/fluorescein-DHPE in the ration 16:4:1; total lipid concentration ~1.6 mM) were put in wells of a 384-well plate. For printing an array of 100 spots, 50 TL of lipid solution was added to four different wells, and the printer was programmed to print twenty five spots from each well. Four wells were used in order to maintain a more uniform dispensation of the lipid over the hundred spots. During the print run, the system was maintained at 100% humidity.

After printing, the substrate was stored in a humid chamber. After 30 min, 200 TL of buffer was added to the surface in close proximity to the printed area, and a microscope cover slip was gently laid onto the surface, ensuring that all printed region was covered with buffer. The substrates were then imaged using a fluorescence microscope (Olympus AX 70 camera, FITC filter) equipped with a CCD detector (Princeton Instruments).

VI. Synthesis of High Density Membrane-Arrays:

FIG. 3 shows fluorescence micrographs of lipids (DPPC/DMPC (4:1), doped with 5% fluorescein-DHPE) printed in an array of 10×10 spots onto a Brij®-derivatized gold surface, followed by incubation of the printed substrate under a solution of phosphate buffer (10 mM, pH 7.6) for 30 min. The patterned nature of the fluorescence indicates that the lipid remains confined to the printed areas. Monitoring of the size of the printed spots by fluorescence microscopy did not show an increase in the spot size over the duration of the experiment (3 h of incubation under buffer). These observations demonstrate the feasibility of this approach for making HDAs of membrane-proteins on the Brij®-derivatized surfaces. The data also suggests that the surface density of the Brij®-molecules is optimal—the density is high enough to facilitate the tight binding of a bilayer-lipid membrane, but is low enough to restrict lateral diffusion of the lipid molecules to within the printed areas. The significance of these data is that it allows the convenient synthesis of membrane arrays on a surface that otherwise satisfies all of the criteria of an idealized lipid binding surface, as described above.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

Other embodiments are within the claims.

We claim:

1. A method for producing a supported membrane comprising the steps of:
   (i) providing a substrate which is selected from the group consisting of gold, silver, platinum, plastic, polymer and glass, and wherein the substrate has a coating of a monolayer having reactive functional groups, wherein the monolayer comprises a thioalkyl compound or a silane compound;
   (ii) activating said reactive functional groups to form an activated monolayer;
   (iii) contacting said activated monolayer with a linker compound wherein the linker compound comprises a straight or branched $C_{10}$–$C_{25}$ alkyl, alkynyl, alkenyl, aryl, araalkyl, heteroalkyl, heteroalkynyl, heteroalkenyl, heteroaryl, heteroaraalkyl molecule comprising:
   (a) a terminal functional group that reacts with the activated monolayer;
   (b) a hydrophilic spacer region; and
   (c) a membrane adhering region;
   to form a derivatized monolayer having covalently bonded linker moieties; and
   (iv) contacting said derivatized monolayer with a membrane solution to produce a supported membrane.

2. The method of claim 1, wherein the substrate is coated with gold.

3. The method of claim 1, wherein the monolayer is a self-assembled monolayer.

4. The method of claim 1, wherein said contacting in step (iv) is done by incubation or printing.

5. The method of claim 4, wherein said contacting in step (iv) is done by printing using a quill-pin printer.

6. The method of claim 1, wherein the thioalkyl compound is selected from the group consisting of a thioalkyl acid, thioalkyl alcohol, thioalkyl amine, and halogen containing thioalkyl compound.

7. The method of claim 6, wherein the thioalkyl compound is a thioalkyl acid.

8. The method of claim 7, wherein the thioalkyl compound is 16-mercaptohexadecanoic acid.

9. The method of claim 1, wherein the silane compound is selected from the group consisting of a silyl anhydride, silyl acid, silyl amine, silyl alcohol, vinyl silane and silyl acrylate.

10. The method of claim 1, wherein the reactive functional group is selected from the group consisting of a carboxylic acid, halogen, amine, thiol, alkene, acrylate and hydroxyl group.

11. The method of claim 10, wherein the reactive functional group is a carboxylic acid.

12. The method of claim 1, wherein the activated functional group is selected from the group consisting of an anhydride, ester, acid halide, isocyanate, hydrazine and maleimide derivative.

13. The method of claim 12, wherein the activated functional group is an anhydride.

14. The method of claim 1, wherein the terminal functional group is selected from the group consisting of a carboxylic acid, halogen, amine, thiol, alkene, acrylate, anhydride, ester, acid halide, isocyanate, hydrazine, maleimide and hydroxyl group.

15. The method of claim 14, wherein the terminal functional group is selected from a group consisting of an amine and a hydroxyl group.

16. The method of claim 1, wherein the hydrophilic spacer region comprises n oxyethylene groups, wherein n=2 to 25.

17. The method of claim 16, wherein the hydrophilic spacer region comprises ten oxyethylene groups.

18. The method of claim 1, wherein the membrane adhering region comprises a straight or branched chain $C_{10}$–$C_{25}$ hydrophobic tail.

19. The method of claim 18, wherein the membrane adhering region comprises a $C_{18}$ straight chain hydrophobic tail.

* * * * *